United States Patent [19]

Boswell, Jr.

[11] 4,212,815
[45] Jul. 15, 1980

[54] PREPARATION OF VINYLENE FLUORIDES

[75] Inventor: George A. Boswell, Jr., Wilmington, Del.

[73] Assignee: E. I. Du Pont de Nemours and Company, Wilmington, Del.

[21] Appl. No.: 922,048

[22] Filed: Jul. 5, 1978

Related U.S. Application Data

[63] Continuation-in-part of Ser. No. 799,124, May 20, 1977, abandoned.

[51] Int. Cl.$^2$ .............................................. C07J 9/00
[52] U.S. Cl. .............................. 260/397.2; 260/397.4; 260/397.5
[58] Field of Search ............... 260/397.2, 239.5, 397.4, 260/397.5

[56] References Cited

U.S. PATENT DOCUMENTS 3,976,691  8/1976  Middleton ......................... 260/239.5

Primary Examiner—Elbert L. Roberts

[57] ABSTRACT

A ketone is reacted with an N,N-disubstituted-aminosulfur trifluoride in the presence of a polar solvent, preferably also in the presence of a polar catalyst, to produce a vinylene fluoride. Exemplary is the reaction of cholestan-3β-ol-6-one-3-t-butyl ether with diethylaminosulfur trifluoride in the presence of fuming sulfuric acid and tetrahydrofuran to produce 6-fluorocholesterol.

9 Claims, No Drawings

PREPARATION OF VINYLENE FLUORIDES

RELATED APPLICATION

This is a continuation-in-part of application Ser. No. 799,124 filed May 20, 1977 and subsequently abandoned.

BACKGROUND OF THE INVENTION

1. Field of the Invention

This invention relates to the preparation of vinylene fluorides by reaction of an N,N-disubstitutedaminosulfur trifluoride with a ketone preferably in the presence of a polar solvent and/or polar catalyst.

2. Prior Art

Vinylene fluorides, i.e. compounds having the group $>C=CF-$, are an interesting class of compounds and their preparation by a direct process would be desirable. They have not been reported as obtainable from sulfur fluorides and organic carbonyl compounds. A few such compounds that have been prepared by other methods, e.g., 5-fluorouracil and Floxuridine [1-(2-deoxy-$\beta$-D-ribofuranosyl)-5-fluorouracil], exhibit potent clinical activity. A method whereby vinylene fluorides could be readily obtained should lead to compounds having unusual chemical and pharmacological properties.

Organic compounds having a carbonyl group have been reacted with fluorinating agents such as sulfur tetrafluoride or an N,N-disubstitutedaminosulfur trifluoride to give the corresponding difluoride [Middleton, *J. Org. Chem.*, 40, 574 (1975); U.S. Pat. Nos. 3,914,265 and 3,976,691 to Middleton; and Markovskij et al., Synthesis, 787 (1973)]. The reaction can be conducted in glass at ordinary pressure and temperature rather than in alloy pressure vessels resistant to corrosion when SF$_4$ is used. In general, the reactions with carbonyl containing compounds and an aminosulfur trifluoride have been conducted in an inert polar or nonpolar solvent.

A few steroid compounds that have a ring fused in a position which is alpha to a ketone group have been reacted with SF$_4$ and the resulting gem difluoride treated with an activated alumina to produce the corresponding vinylene fluoride (see U.S. Pat. No. 3,413,321 to Boswell) as in the equation

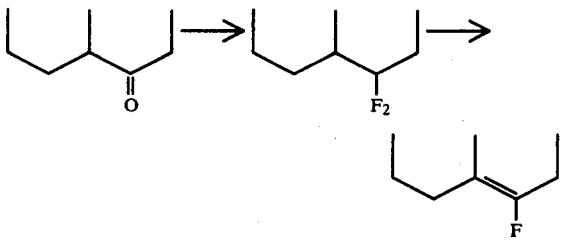

1-Fluorocycloalkenes have also been prepared by this procedure [Strobach and Boswell, *J. Org. Chem.* 36, 818 (1971)].

DESCRIPTION OF THE INVENTION

The invention is the process of reacting a ketone having at least one hydrogen atom on one alpha carbon atom with a disubstitutedaminosulfur trifluoride of the formula

RR$^1$NSF$_3$ wherein each R and R$^1$, alike or different, is a primary alkyl group of 1–4 carbon atoms; or when taken together are $-(CH_2)_4-$, $-(CH_2)_5-$, or $-CH_2CH_2OCH_2CH_2-$;

at a temperature in the range of $-40°$ C. to about $+80°$ C.;

In the presence of an inert polar solvent and preferably in the presence of a polar catalyst, and recovering a compound having a vinylene fluoride, $>C=CF-$, group.

The reaction may be shown as $$R^3R^2CH-\overset{O}{\underset{\|}{C}}-CR^2R^3R^4 + RR^1NSF \longrightarrow$$
$$R^3R^2C=CF-CR^2R^3R^4 + R^3R^2CH-CF_2-CR^2R^3R^4$$

wherein each R$^2$, R$^3$, and R$^4$, alike or different, is H or an organic group, and R and R$^1$ are as defined above.

The starting ketone must have at least one hydrogen atom on an alpha carbon atom since the ethylenic unsaturation cannot form if both carbons alpha to the ketone group are tertiary carbons, i.e. have no hydrogen. The starting ketone preferably is also free of basic amino groups and $\alpha,\beta$-ethylenic unsaturation since these groups and such unsaturation appear to have an inhibiting effect on the desired reaction.

The ketone may be cyclic or acyclic, so long as it has at least one alpha hydrogen atom. Exemplary are acetone, butanone, pentanone, hexanone, cyclobutanone, cyclopentanone, cyclohexanone, cyclododecanone, t-butylcyclohexanone, hydroxycyclohexanone, 4-hydroxycyclohexanone benzoate, methylcyclohexanone, ethylcyclohexanone, ethyl benzoyl acetate, phenyl acetone, cyclohexanedione, chlorocyclopentanone, and the like. Steroids containing a ketone group are also useful in the invention, as for example cholestan-3-$\beta$-ol-6-one-3-t-butyl ether, 6-ketocholestan-3-$\beta$-ol acetate, cholestan-3-one, 5-androsten-3-$\beta$-ol-17-one acetate and the like.

The disubstitutedaminosulfur trifluorides are known compounds and have the formula RR$^1$NSF$_3$ wherein R and R$^1$, alike or different, are primary alkyl radicals of up to 4 carbons; or when R and R$^1$ are taken together they are $-(CH_2)_4-$, $-(CH_2)_5-$ or $-CH_2CH_2OCH_2CH_2-$. Particularly useful are diethylaminosulfur trifluoride, pyrrolidinosulfur trifluoride, morpholinosulfur trifluoride and piperidylsulfur trifluoride.

By inert polar solvent or catalyst is meant compounds that have a high dielectric constant but are nonreactive with the aminosulfur trifluoride or the ketone.

Solvents giving useful conversions of ketones to vinylene fluorides are polar and include dioxane, diethyl ether, tetrahydrofuran, ethylene glycol dimethyl ether, diethylene glycol dimethyl ether, and triethylene glycol dimethyl ether, etc. These contain only C, H and O.

Nonpolar solvents such as hydrocarbons and halogenated hydrocarbons increase the amount of difluoro (gem) compound formed and are not preferred.

The addition of a small amount of a strong acid as a highly polar catalyst, such as fuming sulfuric acid, increases the rate of formation of the desired vinylene fluoride. Other useful catalysts are strong mineral acids that in the quantities used do not react with the carbonyl compound. Hydrogen halides such as hydrogen fluoride tend to add to the vinylidene double bond and are not preferred. Useful catalysts include perchloric, polyphosphoric, fluosulfonic acids, etc. The useful ones generally have a log $k_a$ of more than about $-2$. The amount of catalyst is generally of the order of 0.001 to 1% by weight of the ketone. The catalyst is believed to function to increase the polarity of the reaction media.

The reaction is conducted under substantially anhydrous conditions. The reaction vessel is suitably glass but metal or ceramic containers can be used. The reaction is conducted at $-40°$ to about $+80°$ with the range 15° to 40° being generally preferred. The time is dependent upon the reactants and the temperature with times of from less than an hour to a week or more being useful. Pressure is not critical but ambient or autogenous pressure is preferred.

The vinylene fluoride can be separated from the reaction mixture by conventional procedures. Chromatography is a particularly useful procedure for separation and purification but crystallization, extraction, etc. can be used.

A vinylene fluoride readily obtainable by the process of this invention is 6-fluorocholest-5-en-3β-ol and derivatives which have the formula

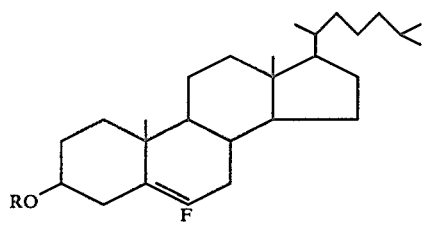

where R is H, alkyl or up to 6 carbons; cycloalkyl of generally 4–10 carbons, e.g., cyclopropylmethyl and adamantyl; tetrahydropyranyl; acyl of up to 18 carbons such as acetyl, decanoyl and 9,12-octadecadienoyl; and aroyl and substituted aroyl such as p-nitrobenzoyl.

In the reaction a cholesterol that has the 3-hydroxyl group protected in a derivative such as ether or acyl is generally employed in the fluorination reaction. The 3-hydroxyl can be obtained by conventional hydrolysis of an acyl or removal of an ether group from the corresponding cholesterol ester or ether.

6-Fluorocholesterol and its 3-ether or acyl derivatives can be used with a liquid crystal mixture of the type described in U.S. Pat. No. 3,409,404 (40% cholesteryl oleyl carbonate, 35% cholesteryl nonanoate and 32% cholesteryl chloride) to shift the color to red. For example, 1% of 6-fluorocholesterol when added to the above mixture shifts the reflection maximum from 5900 Å (green) to 6200 Å (orange) while 2.1% gives a maximum at 6650 Å with a deep red color.

6-Fluorocholesterol has also been found effective to lower serum cholesterol when given at a rate of 4 mg/kg/day for 10 days to 10 male rats fed a high cholesterol diet. The serum cholesterol for a control group was 81 mg/100 ml while those given the 6-fluorocholesterol was 71 mg/100 ml.

6-Fluorocholesterol also forms a digitonide complex with digitonin according to the procedure of Windaus as described by Fieser, *Reagents for Organic Synthesis*, Vol. 2, p. 137. 6-Fluorocholesterol is useful as a precursor to 6-fluoro vitamin D.

SPECIFIC EMBODIMENTS OF THE INVENTION

The following are illustrative examples of the invention in which all parts are by weight and all temperatures are Centigrade unless otherwise stated. All the examples were conducted under essentially anhydrous conditions.

EXAMPLE 1

Reaction of Cholestan-3β-ol-6-one 3-t-Butyl Ether (1) and DAST (Diethylaminosulfur Trifluoride)

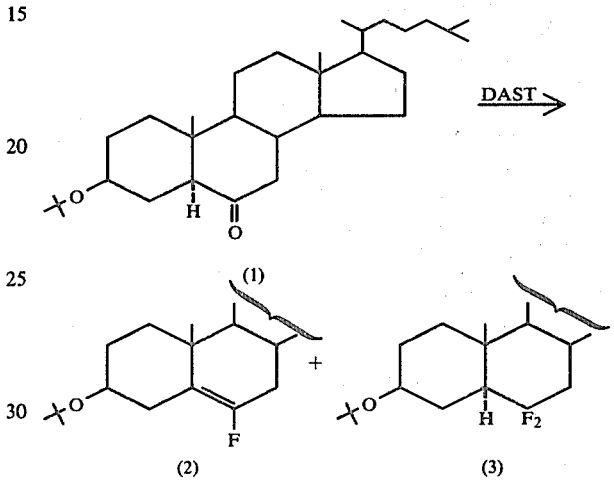

A. A 2.1 g amount of cholestan-3β-ol-6-one 3-t-butyl ether (1) was dissolved in 70 ml tetrahydrofuran (THF) under $N_2$ in a dried Teflon ® bottle with stirring. Ten ml of diethylaminosulfur trifluoride (DAST) was added. The reaction mixture was heated to 50° C. with stirring for 10 days under a nitrogen atmosphere to maintain essentially anhydrous conditions.

The reaction was worked up by pouring into water and extracting with methylene chloride. The extract was washed with saturated $NaHCO_3$, water, and saturated NaCl solution; dried with magnesium sulfate, filtered, and evaporated to yield 1.7 g of tan crystalline solid. This was recrystallized from ethanol-ether: mp 177°–179°, $[\alpha]_D^{25} -36°$ (c 1.0, $CHCl_3$).

The $^{19}F$ nmr spectrum of the crude material indicated 84 mol % vinylene fluoride (2) ($-111.13$ ppm, single peak), 11 mole % of 6,6-difluoride (3) ($-92.92$ and $-107.64$ ppm) and a trace of $\Delta^6$-6-fluoride ($-116.12$ ppm, single peak).

The first crop of recrystallized material (0.8 g) was exclusively vinylene fluoride (2) ($-111.19$ ppm, single peak): HRMS m/e (460.4102) $C_{31}H_{53}FO$. The IR spectrum had a single sharp band at 5.83µ (C=CF).

B. To serve as a contrast, Example 1 was repeated using no solvent and then again using a nonpolar solvent. The amount of vinylene fluoride compound (2) obtained was reduced in both instances.

| Solvent | Mol % of (2) produced |
| --- | --- |
| 1. None | 63 |
| 2. $CH_2Cl_2$ | 40 |

EXAMPLE 2

Reaction of 6-Ketocholestan-3β-ol Acetate (4) and DAST

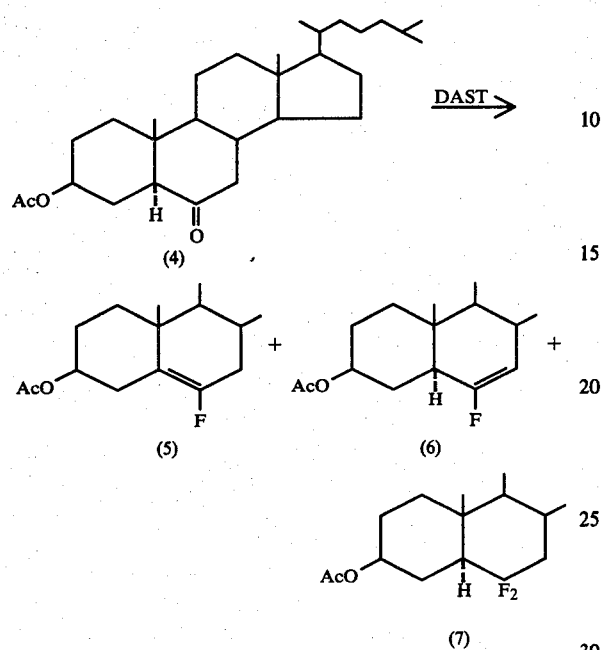

A. To a magnetically-stirred solution of 6-ketocholestanyl acetate [(4), 8.0 g] and glyme (100 ml) containing 2 drops of 25% fuming sulfuric acid in a Teflon® bottle was added 20 ml of DAST. The resultant homogeneous solution was allowed to stir for 17 days at 50° under $N_2$ until thin layer chromatography (TLC) indicated the reaction was complete. The yellow reaction solution was slowly poured into a mixture of ice and 5% sodium bicarbonate solution (Caution-Foaming) with vigorous stirring. The precipitated solid was collected on a filter, rinsed well with water, and dried to yield 6.39 g (~80%) of light tan solid. This material based on $^{19}F$ nmr is 82% (5), 8% (6) and 8% (7). The yield is less than theoretical because aliquots had been removed prior to the final workup, which were used to determine the degree of completeness of the reaction. Recrystallization from methanol gave colorless flat needles, yield 5.83 g, mp 95°–100° (bright color change on melting). The analytical sample was recrystallized twice from methanol: mp 110°–112°, $[\alpha]_D^{25} -36°$ (c 1.01, CHCl$_3$); $^{19}F$ nmr (94.1 MHz), (CDCl$_3$/F-11) $\phi^* -109.15$ ($\Delta^5-6F$), $-116.13$ ($\Delta^6-6F$). Integration indicates the material to be 94–95% 6-fluorocholesterol acetate (5) containing 5–6% of the $\Delta^6$-isomer (6).

Anal. Calcd. for $C_{29}H_{47}FO_2$ (446.36): C, 78.2; H, 10.5; F, 4.25

Found: C, 77.79, H, 10.49; F, 4.26 78.17 10.55 4.30

B. A portion of above crude reaction product [about 82% 6-fluoro-5-cholesten-3β-ol acetate (5)] was dissolved in 100 ml of methanol, 20 ml of conc. HCl added and the resultant mixture heated at reflux for 1 hour. On cooling a white crystalline solid precipitated, which was collected on a filter, washed with water, and air dried, mp 130°.

The infrared spectrum was identical to 6-fluorocholesterol prepared by alumina-dehydrofluorination of 6,6-difluorocholestan-3β-ol t-butyl ether; $\lambda_{max}^{Nujol}$ 3.07 (OH), 5.83 (C=C—F), 9.42μ (C—OH). A small amount of 6-fluoro-6-ene (6) isomer could be detected in the infrared spectrum. Recrystallization from methanol of 0.46 g gave 0.366 g of white crystalline product:

mp 128°–130°; $[\alpha]_D^{25} -34°$ (c 1.00, Chf); $^{19}$Fnmr, δ, ppm (94.1 MH$_3$, CDCl$_3$/F-11) 110.3 (d,$J_{HF}$~6H$_3$)

Anal. Calcd. for $C_{27}H_{45}FO$ (404.34): C, 80.14, H, 11.21; F, 4.69

Found: C, 79.66; H, 11.24; F, 4.61 4.59

A highly purified sample (high pressure liquid chromatography) had the following physical constants:

mp 139.5°–140°; $[\alpha]_D^{24} -39°$ (c 1.1, CHCl$_3$);

Anal. m/c (175°) ($C_{27}H_{45}FO$) 404.3444; Raman Δ 1715 cm$^{-1}$ (C=C—F).

EXAMPLE 3

Reaction of Cholestan-3-one and DAST

When the general procedure of Examples 1 and 2 was followed but with cholestan-3-one, the following equation and table show the effect of polar solvent on vinylene fluoride formation. The relative mole percent yields were calculated on the $^{19}F$ nmr.

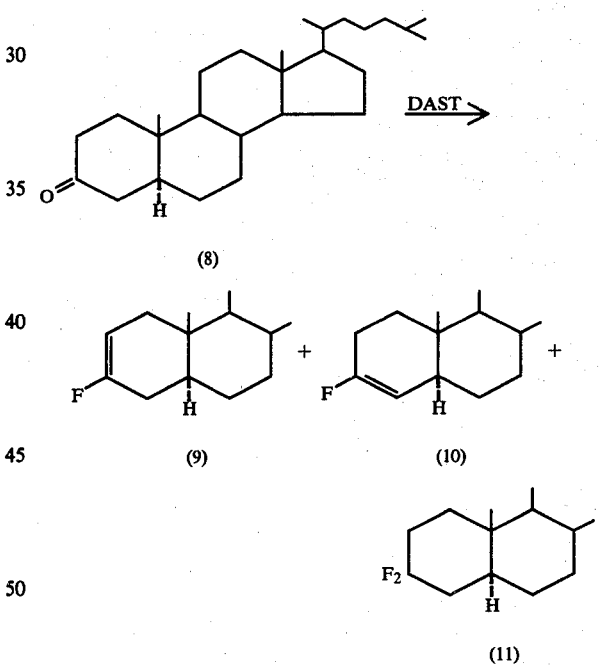

The conditions for the reaction and the yields are set out below:

| | | | | Mole % of Compound | | |
|---|---|---|---|---|---|---|
| Ex. | Solvent | Polar Catalyst | Temp. °C. | Days | (9) | (10) | (11) |
| 3(a) | glyme | H$_2$SO$_4$/SO$_3$ (2 drops) | 50 | 6 | 49.1 | 16.4 | 34.4 |
| 3(b) | CH$_2$Cl$_2$ | — | room temp. | 4 | 4.5 | 2 | 93.5 |
| 3(c) | glyme | — | 50 | 9 | 29 | 16 | 55 |

EXAMPLE 4

5-Androsten-3β-ol-17-one Acetate and DAST

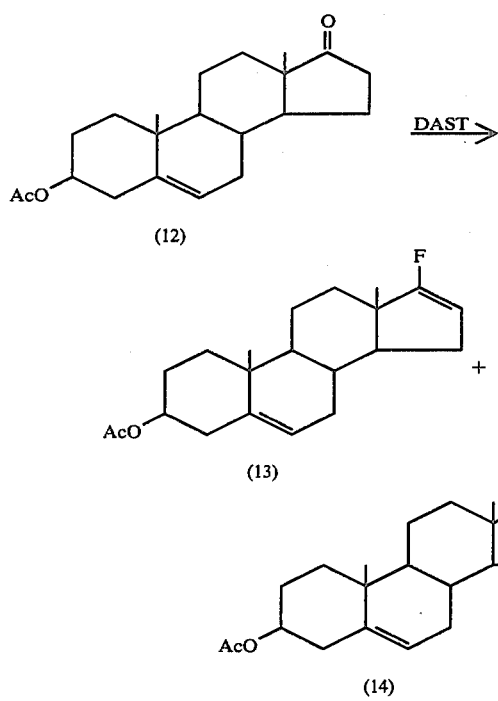

A. The compound (12), 4 g, was mixed with 4.1 g of DAST in the presence of 25 ml glyme as solvent and 0.3 ml of fuming sulfuric acid and stirred at 50°–60° C. for 9 days under anhydrous conditions.

The reaction mixture at the end of that time showed the presence of 82 mol % of (13) and 18 mol % of (14). The $^{19}F$ nmr, δ, ppm data for these compounds were:

| (13) | (14) |
|---|---|
| −131.80 | −101.32 |
|  | −103.65 |
|  | −114.25 |
|  | −116.59 |

The IR spectrum for compound (13) was 6.05μ (C=CF).

B. When reaction (A) above was repeated without solvent or polar catalyst the only product obtained was the difluoro (gem) compound (14).

EXAMPLE 5

Reaction of 4-t-Butylcyclohexanone and DAST

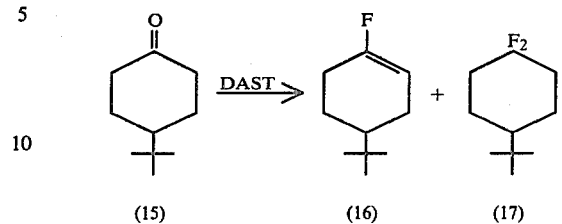

A. A 20.0 g amount of 4-t-butylcyclohexanone was dissolved in 230 ml of glyme at room temperature in a dried Teflon ® bottle under $N_2$, with stirring. Five milliliters of 20% fuming sulfuric acid was added and the mixture was stirred for 5 min. Forty milliliters (44.4 g) of diethylaminosulfur trifluoride was added. The resultant mixture was stirred at ambient temperature under $N_2$ for 24 hours.

The mixture was poured into dilute $NaHCO_3$ solution and extracted with methylene chloride. The extract was washed with saturated $NaHCO_3$, $H_2O$ and saturated NaCl, dried over $MgSO_4$, filtered and carefully evaporated to give 18.4 g of light tan liquid.

The crude product was loaded in hexane onto a chromatography column of 600 g of Silicar CC-7 in hexane. Elution with hexane brought off all fluorinated products in 5 fractions (15.9 g). The $^{19}F$ nmr spectra indicated that the fluorinated compounds were 82 mol % of 4-t-butylcyclohexenyl fluoride (16) and 18 mol % gem-difluoride (17). The first two fractions (totalling 12.0 g), were 95% of compound (16). Further elution with methanol brought off 2.5 g consisting of starting material and two unknown impurities.

$^{19}F$ nmr spectrum: vinyl fluoride-singlet at −104.84 ppm

Gem-Difluoride singlets at =90.81 ppm and −93.30 ppm.

Yield 92%.

Conversion 86.4%. High Resolution Mass Spectroscopy: (Fraction #2) measured m/e 156.1323, Calcd: 156.1313 $C_{10}H_{17}F$; No detectable gem-difluoride Anal. Calcd. for $C_{10}H_{17}F$: C, 76.8; H, 10.8; F, 12.2. Found: C, 76.64; H, 10.97; F, 12.23 76.56 11.16.

B. In a series of reactions 4-t-butylcyclohexanone was reacted with DAST under varying conditions as indicated in the table below.

| Ex. | Solvent | Ratio[a] of DAST/Ketone | Temp. | Time Days | Mol % Compound (16) | (17) | % Conv.[b] | Yield[c] |
|---|---|---|---|---|---|---|---|---|
| (1) | — | 5.60 | ambient | 6 | 15 | 85 | 100 | — |
| (2) | $CCl_3F$ |  | ambient | 2 | 37 | 63 | 93 | 90 |
| (3) | p-dioxane | 0.43 | ambient | 2 | 49 | 51 | 100 | 85 |
| (4) | ethyl ether | 1.96 | 35° C. | 40 | 46 | 52 | 100 | 88 |
| (5) | ethyl acetate | 1.95 | 50° C. | 2 | 44 | 56 | 100 | 100 |
| (6) | THF | 0.98 | ambient | 5 | 44 | 56 | [d] | — |
| (7) | glyme |  | ambient | 2 | 56 | 44 | 99 | 90 |
| (8) | glyme |  | 50° C. | 2 | 43 | 57 | 100 |  |
| (9) | glyme |  | ambient | 2 | 33 | 67 | 100 |  |

-continued

| Ex. | Solvent | Ratio[a] of DAST/Ketone | Temp. | Time Days | Mol % Compound (16) | (17) | % Conv.[b] | Yield[c] |
|---|---|---|---|---|---|---|---|---|
| (10) | glyme | | ambient | 2 | 67 | 33 | 33 | |

[a] weight to weight basis
[b] % of ketone reacted that was not recovered
[c] % of ketone reacted
[d] reaction incomplete The results in Examples (3) through (10) in the table immediately above show that the production of 4-t-butylcyclohexenyl fluoride (16) is favorably influenced when a polar solvent is used.

EXAMPLE 6

Reaction of 4-Hydroxycyclohexanone Benzoate and DAST

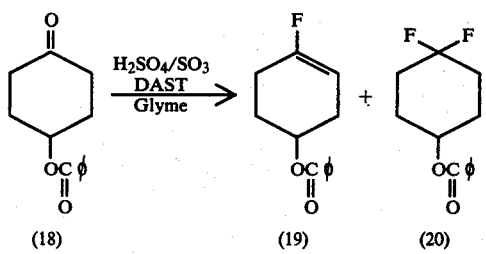

A. Four g of 4-ketohydroxycyclohexanone benzoate (18) (0.018 moles) was dissolved in 25 ml glyme under $N_2$ in a stirred Teflon ® bottle. Added 0.5 g 20% fuming sulfuric acid, stirred for 5 min, the added 5.6 g DAST (0.04 moles) and stirred at room temperature for 48 hours.

The reaction mixture was worked up after 48 hrs by pouring into dilute $NaHCO_3$ solution and extracting with $CH_2Cl_2$, washing the extract with $H_2O$, with saturated NaCl, drying with $MgSO_4$, filtering and evaporating under vacuum to yield 5.2 of yellow oil. IR shows some ketone was still present.

The crude product was distilled through a spinning band column. The main fraction boiled at 76° C. head temperature (1 mm Hg pressure). Material which crystallized in the head was heated periodically to get it to flow. Yield, 2.4 g of a light yellow oil which partially crystallized.

$^{19}F$ nmr: Product is 82.2 mol % vinylene fluroide (19), 17.8 mol % difluoride (20).

$^{19}F$ nmr, δ, ppm: Vinylene fluoride: Single peak decoupled at −102.33 ppm. Difluoride 4 peaks, 2 strong, 2 weak, at −93.32 ppm, −95.84 ppm, −100.28 ppm, very weak one at −102.94.

B. When the fluorination was carried out using methylene chloride as the solvent, the product was 35 mol % vinylene fluoride (19) and 65 mol % of gem-difluoride (20).

EXAMPLE 7

Reaction of 2-Methylcyclohexanone and DAST

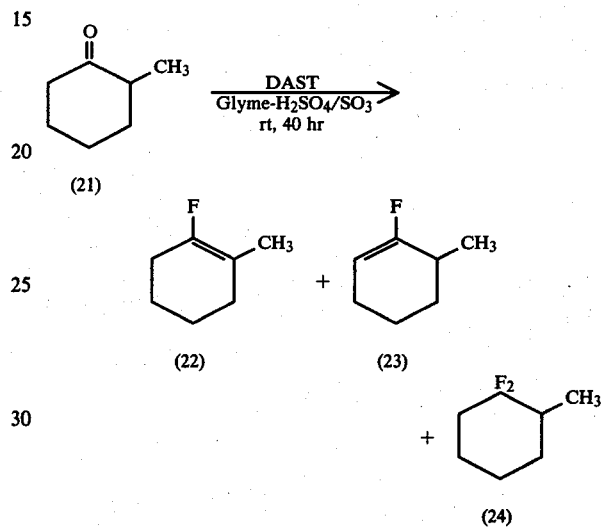

A. To a solution of 2-methylcyclohexanone (21) (4.0 g, 0.0357 moles) in diglyme (40 ml) in a dried Teflon ® bottle equipped with magnetic stirrer under $N_2$, there was added 20% fuming sulfuric acid (1 ml) followed by DAST (11.0 g, 0.079 mole). After stirring for 40 hours at ambient temperature, analysis of an aliquot by G. C. (gas chromatography) indicated 100% conversion of ketone (21) had been achieved and that three products had been formed. The reaction mixture was carefully poured into a stirred mixture of ice and 5% sodium bicarbonate solution. Extraction with a minimum volume of methylene chloride and washing the organic layer with saturated $NaHCO_3$ solution, drying over anhydrous $MgSO_4$ and filtering, gave a solution of vinylene fluorides (22) and (23) and gem-difluoride (24) in 65, 10.5, and 24.5 mole percent by $^{19}F$ nmr (−110.65, −110.14, and −96.21, −98.71, 115.55, 118.06 ppm, respectively). A portion of the methylene chloride solution was analyzed by HRMS.

HRMS m/e (134.0914) $C_7H_{12}F_2$ and (114.0855) $C_7H_{11}F$, molecular ions.

B. When the above procedure was repeated, the following table shows the amount of vinylene fluorides (22) and (23) obtained compared to the amount of difluoride under varying conditions of solvent and/or acid catalyst. In Example (2) the conversion was incomplete after 40 hours.

| No. | Conditions | Mole % (22) | (23) | (24) |
|---|---|---|---|---|
| (1) | Glyme, $H_2SO_4/SO_3$ | 67 | 11 | 22 |
| (2) | Glyme, no acid | 36 | 13 | 51 |
| (3) | $CH_2Cl_2$ | 30 | 10 | 60 |

-continued

| No. | Conditions | Mole % | | |
|---|---|---|---|---|
| | | (22) | (23) | (24) |
| (4) | Glyme, trace (2 drops) of H$_2$SO$_4$/SO$_3$ | 53 | 13 | 34 |
| (5) | Triglyme, H$_2$SO$_4$/SO$_3$ | 69 | 7.5 | 23.5 |

EXAMPLE 8

Reaction of Cyclododecanone and DAST

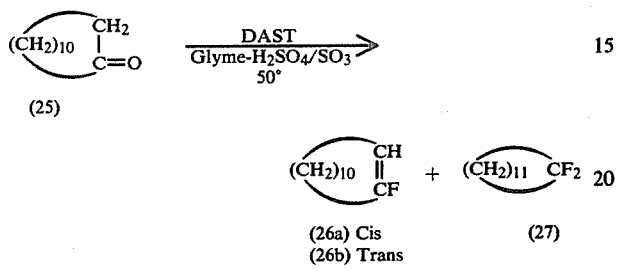

To a stirred solution of cyclododecanone (25) (5.5 g) and glyme (25 ml) under N$_2$ was added 20% fuming sulfuric acid (0.5 ml) followed by DAST (11 g). The reaction mixture was allowed to stir for 5 days at room temperature during which time approximately 50% conversion had been achieved based on G.C. analysis. The temperature was increased to 50°. After 6 days the starting ketone (25) was consumed.

The product was isolated with methylene chloride in the usual manner, yielding 5.4 g of a dark oil. $^{19}$F nmr indicated this to be 43.3, 20.1, and 36.5%, respectively of gem-difluoride (27) and vinylene fluorides (26a) and (26b). This was purified by column chromatography on Silicar CC-7 packed in hexane. Elution with hexane gave 2.4 g of a light yellow oil in the 1st fraction. $^{19}$F nmr spectral analysis indicated it to consist of 34% gem-difluoride (27), 22% cis-vinylene fluoride (26a), and 44% trans-vinylene fluoride (26b). Analysis by G.C. and thin layer chromatography showed product to contain 3 components. A portion of the mixture was separated into pure cis- and trans-vinyl fluorides (26a) and (26b) by high pressure liquid chromatography (HPLC) using the Waters Associates instrument.

| Fraction No. | Mol % Difluoride | Mol % Vinylene Fluoride | | Wt, Grams |
|---|---|---|---|---|
| | | cis | trans | |
| 2 | 94 | 5 | 1 | 0.2 |
| 3 | 5 | — | 95 | 0.3 |
| 4 | 4.5 | 66.5 | 29 | 0.2 |
| 5 | trace | 17 | 83 | 0.3 |

EXAMPLE 9

When the general procedure of Example 7 was repeated except that cyclohexanone was used, 73 mol % of 1-fluorocyclohexane and 27 mol % of 1,1-difluorocyclohexane results.

Cycloheptanone under these conditions gave only a small amount of the 1-fluorocycloheptene. When nuclear substituents are present on the cyclopentanone, the relative amount of the unsaturated monofluoride increases.

EXAMPLE 10

Ethyl Benzoyl Acetate and DAST

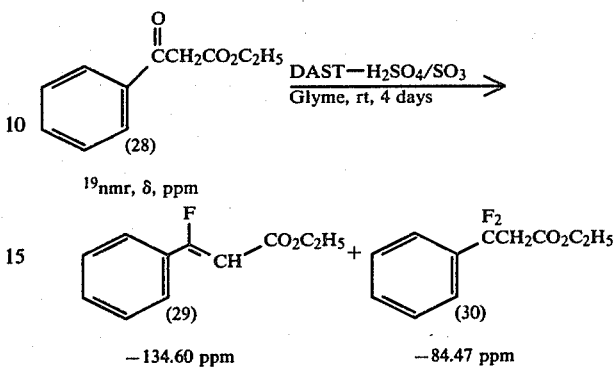

The ratio of vinylene fluoride (29) to gem-difluoride (30) was 17.9:2.2 based on $^{19}$F nmr.

EXAMPLE 11

Phenyl Acetone and DAST

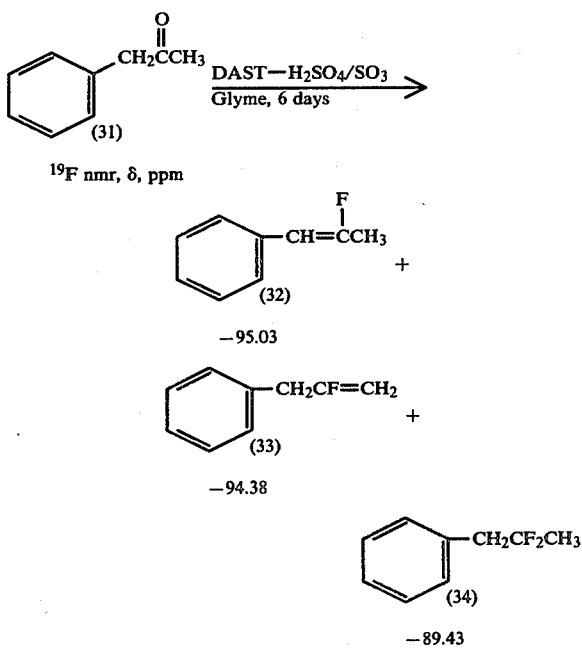

The ratio of the vinylene fluoride (32) to gem-difluoride (34) was about 1:1. A trace amount of the non-conjugated vinylene fluoride (33) was detected.

EXAMPLE 12

2-Hydroxycyclohexanone and DAST

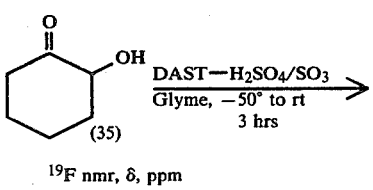

$^{19}$F nmr, δ, ppm

-continued

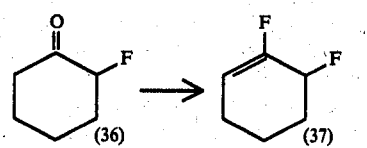

−116.02
(J = 29.5 Hz)
−175.9
(J = 30 Hz)

The product was essentially all (37).

EXAMPLE 13

Cyclohexane-1,4-dione and DAST

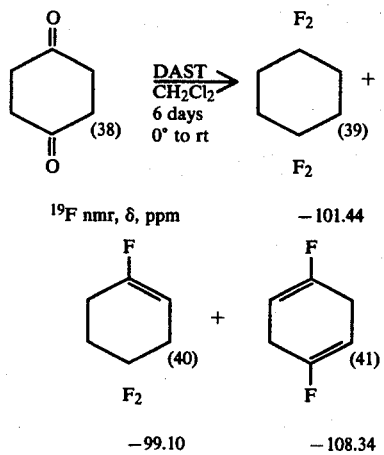

$^{19}$F nmr, δ, ppm     −101.44

−99.10          −108.34          −105.19

A. The ratio of (39) to (40) to (41) was 1.25:1.0:0.08 based on $^{19}$F nmr of the distilled product, which was a mixture of white solid and a colorless liquid.

B. When tetrahydrofuran was used as the solvent, after 10 days at room temperature, the ratio of (39) to (40) to (41) was 1:2.85:0.32.

C. With triglyme and fuming sulfuric acid catalyst for 2 days, all of the dione reacted to give a ratio of (39) to (40) to (42) of 1:3.1:1:2.3. The tetrafluorocyclohexane crystallizes from the reaction mixture and can be separated from the fluorides containing a carbon to carbon double bond since the vinylene fluorides are liquid.

EXAMPLE 14

4-Hydroxycyclohexanone Benzoate and DAST

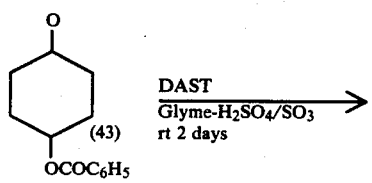

$^{19}$F nmr, δ, ppm

-continued

(44) (82.2%) −102.33

(45) (17.8%) −93.32, −95.84 −100.28, −102.94

EXAMPLE 15

2-Chlorocyclopentanone and DAST

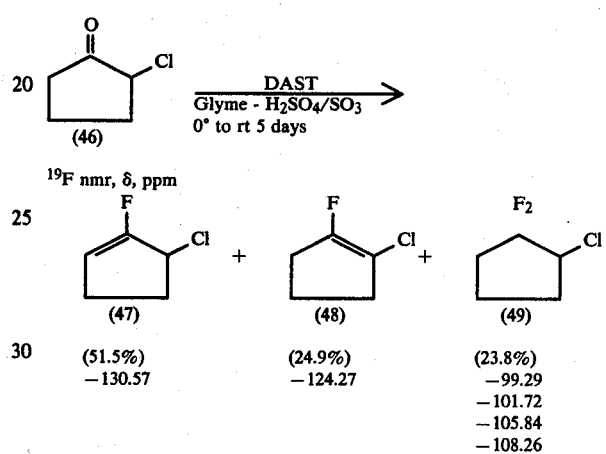

(47) (51.5%) −130.57

(48) (24.9%) −124.27

(49) (23.8%) −99.29 −101.72 −105.84 −108.26

EXAMPLE 16

4-Heptanone and DAST

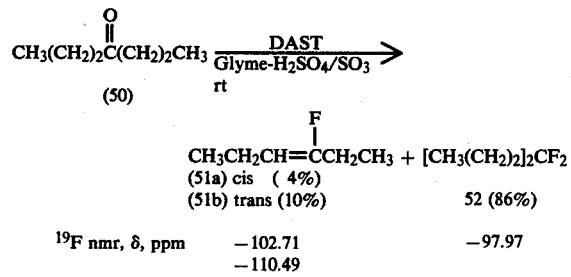

$CH_3CH_2CH=CCH_2CH_3$ + $[CH_3(CH_2)_2]_2CF_2$
(51a) cis (4%)
(51b) trans (10%)                    52 (86%)

$^{19}$F nmr, δ, ppm   −102.71         −97.97
−110.49

Cyclobutanone reacts with diethylaminosulfur trifluoride to produce a vinylene fluoride in glyme solvent and fuming sulfuric acid as catalyst. The major product has the ring opened, i.e., $CH_2=CFCH_2CH_2F$ while some 1,1-difluorocyclobutane is formed.

In reactions of the above, some of the gem difluorides may also be formed and can be separated in the usual manner.

For those starting materials that have unprotected hydroxyl, phenolic, or amino groups (which are generally readily fluorinated by the sulfur fluoride reagent), it may be necessary to use blocking groups to protect them. In general, alcohols are protected as acetates or t-butyl ethers, secondary amines as trifluoroacetamides, and tri-substituted amines as hydrofluoride salts. The hydrofluorides may form in situ by exchange with the hydrochloride, if the hydrochloride salt is used. The

I claim:

1. In an improved process for preparing a vinylene fluoride, the improvement comprising reacting under substantially anhydrous conditions in an inert polar solvent at a temperature of $-40°$ C. to about $+80°$ C. a ketone having at least one hydrogen atom on an alpha carbon atom and a disubstitutedaminosulfur trifluoride of the formula $RR^1NSF_3$ wherein each R and $R^1$, alike or different, is a primary alkyl group of 1–4 carbon atoms, or when taken together R and $R^1$ are $-(CH_2)_4-$, $-(CH_2)_5-$ or $-CH_2CH_2OCH_2CH_2-$, and recovering a vinylene fluoride.

2. The process of claim 1 in which the ketone is free of basic amino groups and $\alpha,\beta$-ethylenic unsaturation.

3. The process of claim 2 conducted in the presence of about 0.001% to 1% by weight of the ketone of an acid having a log $K_a$ of more than about $-2$.

4. The process of claim 2 wherein the polar solvent is tetrahydrofuran.

5. The process of claim 2 wherein the polar solvent is ethylene glycol dimethyl ether.

6. The process of claim 2 wherein the ketone is cyclic.

7. The process of claim 2 wherein the ketone is 6-ketocholestan-3$\beta$-ol-acetate.

8. The process of claim 2 wherein the aminosulfur trifluoride compound is N,N-diethylaminosulfur trifluoride.

9. The process of claim 3 in which the acid is fuming sulfuric acid.